United States Patent [19]

Nohl

[11] Patent Number: 5,010,921

[45] Date of Patent: Apr. 30, 1991

[54] NONSYMMETRICAL VALVE

[75] Inventor: Andre Nohl, San Jose, Calif.

[73] Assignee: Spectra-Physics, Inc., San Jose, Calif.

[21] Appl. No.: 380,827

[22] Filed: Jul. 17, 1989

[51] Int. Cl.$^5$ .......................... F16K 11/74; F16K 3/08
[52] U.S. Cl. ............................ 137/625.46; 137/625.11
[58] Field of Search ...................... 137/625.12, 625.11, 137/625.46, 625.15, 1

[56] References Cited

U.S. PATENT DOCUMENTS

| | | | |
|---|---|---|---|
| 937,406 | 10/1909 | Beardsley | 137/625.11 X |
| 1,348,123 | 7/1920 | Muth | 137/625.11 |
| 3,422,848 | 1/1969 | Liebman et al. | 137/625.15 |
| 3,570,536 | 3/1971 | Walker et al. | 137/625.11 |
| 4,049,020 | 9/1977 | Neveux | 137/625.11 |

Primary Examiner—Arnold Rosenthal
Attorney, Agent, or Firm—Skjerven, Morrill, MacPherson, Franklin & Friel

[57] ABSTRACT

A conventional injection valve, such as used in high performance liquid chromatography apparatus, having six ports and three channels for connecting the ports in two different positions, is modified so that one of the channels is longer than the other two. In this way, when the valve is switched to the load position, one of the ports is always connected to the channel prior to the other port being connected. This improvement in the valve makes the valve more accurate and reduces undesirable mixing of sample and mobile phase in the valve when injecting small quantities of sample.

4 Claims, 6 Drawing Sheets

NONSYMMETRICAL VALVE

BACKGROUND OF THE INVENTION

1. Field of the Invention

This invention relates to an injection valve. Specifically the invention relates to a modified injection valve for use in testing apparatus.

2. Description of the Prior Art

Injection valves are well-known in the prior art. Typical of these sorts of valves are six-port valves as are typically used in conjunction with high performance liquid chromatography (HPLC) apparatus. One example of this type of valve is the Rheodyne 7010 valve, commercially supplied by Rheodyne of Cotati, California. This is a typical sixport valve 10 as shown schematically in FIG. 1A. The valve has six ports 1, 2, 3, 4, 5, 6. A sample loop 12 connects two of the ports, port 1 and port 4. In use, one of the ports, port 6, is connected by tubing 14 to a syringe 16 which is used to suction a sample fluid from a container 18 via a needle (or alternatively a dip tube) 20 and tubing 22 into port 5 and into the valve 10. One of the other ports, port 3, is typically connected to a pump 24 via tubing 26 for providing mobile phase (i.e., liquid) from reservoir 28 via tubing 30 under pressure, and another port, port 2, is typically connected to a liquid chromatography column 32 by tubing 34.

Typically a valve such as valve 10 holds a volume of a few microliters in the sample loop 12. The Rheodyne 7010 valve in one version holds a volume of about seven microliters because the steel tubing which forms loop 12 is about .3 millimeter (.012 inch) inside diameter. Even smaller volumes can be used by providing a smaller diameter tubing in the loop 12. As shown in FIG. 1A, the valve 10 is in the load position (as shown by the arrow) for filling the sample loop. Injection valves such as this one when in the load position transfer quantities of a sample at atmospheric pressure from the sample reservoir 18 to the loop 12. The loop 12 is then connected by throwing the valve to the inject position to the high pressure mobile phase stream from pump 24, which carries the sample into the column 32.

Such a valve thus has two positions. The first position is the load position as shown in FIG. 1A. The second position is the inject position as shown in FIG. 1B. In the load position (FIG. 1A), port 4 is connected to port 5, port 1 is connected to port 6, and port 2 is connected to port 3 as shown. In the inject position (shown schematically in FIG. 1B), port 5 is connected to port 6, port 1 is connected to port 2, and port 3 is connected to port 4.

This two position action of the valve is accomplished due to the interior structure of the valve as shown in FIG. 2. FIG. 2 is an exploded view of the valve 10. As shown, the valve body 40 is typically metal such as stainless steel and contains six small cavities which are the ports 1, 2, 3, 4, 5, and 6. Each of these ports is connected by a passage such as passage 41 to a fitting such as 42 on the other side of the valve body 40 to which the tubing (not shown) is connected, leading to the various elements of the system (not shown) such as the pump, column, syringe, sample needle (or dip tube) and loop. Fitting on to the valve body 40 containing the six ports is a typically plastic rotor 46. This rotor 46 contains four mounting holes 48A, 48B, 48C, 48D for attaching a handle for moving rotor 46 in rotary fashion when the valve 10 is operated In the rotor 46 are three small equally spaced grooves or channels 50A, 50B, 50C, each of which forms approximately 60° of a circle. These channels 50A, 50B, 50C serve to connect the various ports 1, 2, 3, 4, 5, 6. Thus in a first position the channels 50A, 50B, 50C connect the ports 1, 2, 3, 4, 5, 6 in the inject position; when rotated approximately 60° to a second position, the channels 50A, 50B, 50C connect the ports 1, 2, 3, 4, 5, 6 in the load position For most applications, such a valve 10 is satisfactory when used for suction loading as described above where a sample is sucked out of a container by a needle or dip tube. However, in some cases, the performance of such a valve is less than desired.

One of the causes of a performance that is not adequate is due to liquid compressibility. At the head of column 32 the pressure (see FIG. 1A) in an HPLC apparatus is in the range of a few hundred pounds per square inch to 6,000 pounds per square inch. In that range, liquids are compressible. With a typical water/methanol based mobile phase, the compressibility of the mobile phase fluid is around one percent at 1,000 pounds per square inch pressure.

The sample loop 12 volume in a valve 10 can vary from five microliters to several hundred microliters, depending on the volume of the loop 12. To make the valve 10 flexible for use, a volume of 5–100 microliters is a typical choice of ranges of loop 12 volume. With a 100 microliter loop 12 and a pressure of around 2,000 pounds per square inch, the expansion of the mobile phase is around two microliters when going from 2,000 pounds per square inch to atmospheric pressure, due to the typical compressibility of the above-described mobile phase.

It is known in the art to use an injection valve to meter a volume of fluid smaller than the capacity of the valve loop 12. This is done by only partially filling the loop 12 with the sample fluid.

When an injection is made using the valve 10, the fluid inside the loop 12 is put under pressure; this pressure is the column 32 head pressure. The loop 12 of the injection valve 10 remains at that pressure during the analysis run time of the liquid chromatography column 32. When a new injection is to be made, the valve 10 is returned first to the load position. The mobile phase of the loop 12 is then returned to atmospheric pressure, causing expansion of the volume of the mobile phase in the loop 12.

When the valve is rotated into its load position, channel 50C and 50A in the valve rotor connect the ends of the loop 12 (i.e., ports 1 and 4) to respectively the syringe port 6 and needle port 5 of the valve 10. Because of the symmetry of the valve 10, (i.e., the symmetry of the channels 50A, 50B, 50C) ports 1 and 6 should be connected together at the same time as are ports 4 and 5, but because of mechanical tolerances in the forming of the channels 50A, 50B, 50C during manufacturing, one set of ports often connects before the other.

The expansion of the mobile phase occurs either towards the needle port 5 first or towards the syringe port 6 first and then towards the needle port 5. It has been observed that when the valve 10 switches to the load position, a pressure pulse occurs in the tubing 14 connected to the syringe or the tubing 22 connected to the needle (or dip tube) 20. The concern then is what is the affect of the pressure pulse in the expansion of the liquid on the precision and accuracy of the valve 10.

Typically when the loop 12 is first connected to the syringe port 6, a large and reproducibly noticed pressure pulse is observed at each injection. The liquid in the tubing 14 moves back and forth during the expansion of the liquid. The back motion is due to the first expansion of the loop through port 6 (which in that case opens first). The forth motion occurs when port 5 gets connected to the needle port 5 allowing the liquid to expand towards the outside of the system.

At a typical condition with a 20 microliter loop and an HPLC column 34 head pressure of 1,600 pounds per square inch and a loop 12 filled with a volume of sample down to one microliter, there is no visible difference between two modes of use of the valve. That is, the first mode is when the loop 12 is connected first to the needle port 5 and the valve 10 is rotated to the load position and the second mode is when the loop is first connected to the syringe port 6, when the valve 10 is rotated to the load position.

However, for a very small volume of sample into loop 12, such as under one microliter in the case where the amount injected is in the "normal" mode, that is the pulse and pressure is toward the needle port 5, the amount injected is smaller than when the pulse is towards the syringe port 6. When the pressure pulse and expansion is oriented towards the needle port 5, nothing happens on the syringe port 6 side. The inner face of the sample mobile phase at the end of the loop 12 adjacent to port 1 does not move, and when the sample is loaded, the correct amount of sample is loaded into the loop 12.

In the reverse mode, when the pressure pulse is relieved towards the syringe port 1, the sample/mobile phase interphase is perturbed by the back-and-forth motion of the liquid.

Some mixing of the sample and mobile phase undesirably occurs due to the velocity profile in the loop 12 tubing, changes in direction of the fluid, and the possible internal diameter changes of the loop 12 tubing. Because of that mixing, some sample enters the loop 12 before the sample is even pushed into the loop 12. This increases the volume of the sample injected. This problem is visible only when the sample volume injected is small (typically a volume of less than one microliter). If the volume is larger, then the effect of this mixing problem is generally not visible because the entire mixed area in the valve 10 is transferred into the loop 12.

With commercially available valves, due to the mechanical tolerances in the construction of such valves, either the syringe port 6 or the needle port 5 may be connected first. It has been found that amongst typical commercially available valves, some connect the syringe port 6 first, and some connect the needle port 5 first. Thus, accuracy of such valves for small sample volumes is negatively impacted due to inconsistency in the size of the sample measured by the valve. With the typical prior art injection valve, it is difficult or impossible to accurately measure and inject small volumes such as one microliter or less due to this problem of mixing.

SUMMARY OF THE INVENTION

In accordance with the invention, one port in a transferring device such as a valve is connected before a second port is connected.

In the preferred embodiment of the invention, for a rotary injection valve, one of the channels in the valve is made slightly longer than the other two channels in order to ensure that the loop is always relieved (i.e., discharged) towards one of the valve ports. With this modification to the valve, precision (i.e., replicability of sample size) is the same as in the prior art valves. The chief advantage of the invention is that accuracy in delivering small sample volumes is substantially increased. It is possible given the modified valve to deliver sample volumes under .2 microliters. The prior art valve is not capable of delivering such small sample volumes. This is important if in the process of filling the loop, the sample is brought next to the valve when the loop is still under pressure and the valve switched into the load position afterwards. What this means is that the problem appears when a mode of operation such as a "push loop" (see co-pending U.S. Pat. application Ser. No. 07/248,832, filed on Sept. 23, 1988, now abandoned, and U.S. Pat. application Ser. No. 07/467,299, a continuation filed on Jan. 11, 1990, now issued as U.S. Pat. No. 4,957,009 on Sept. 18, 1990) or a similar mode of operation is used. The "push loop" operation allows accurate metering of the sample directly into the loop without carrying the metered sample along any portion of the tubing in the system.

In a preferred embodiment, the invention is used with a typical six-port valve used for suction loading (using a needle or a dip tube to suction sample fluid from a container) which has been modified to have one channel longer than the one of the other. The invention is applicable to any kind of six-port valve. It is also applicable to other types of valves having more than six ports or fewer than six ports, such as four ports. The effect of the modification to the valve in accordance with the invention is to ensure that one port is always connected first when the valve is switched to the load position. In the preferred embodiment, the lengthening of the channel is such that when the valve is installed, the sample loop in the valve will connect to the needle side (i.e., sample) before it connects to the syringe side (i.e., suction) when the valve is switched to load.

While the preferred embodiment is used in conjunction with HPLC equipment, other applications are also in accordance with the invention.

BRIEF DESCRIPTION OF THE DRAWINGS

Similar reference numbers on various figures denote similar or identical structures.

DETAILED DESCRIPTION OF THE INVENTION

Figure 3:
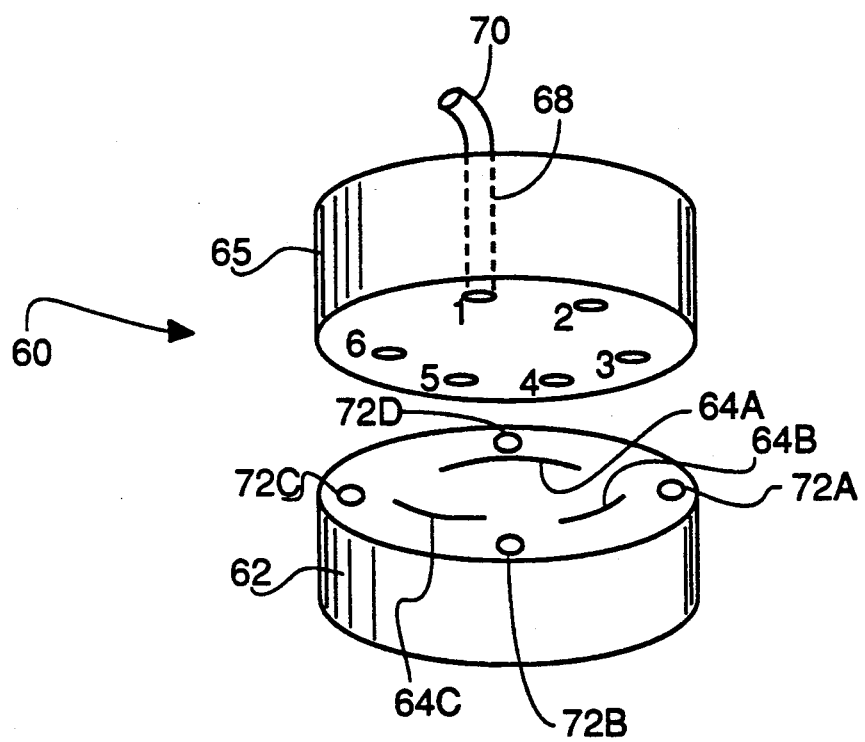
FIG. 3 shows a valve in accordance with the invention.

The valve 60 in accordance with the preferred embodiment of the invention is shown in FIG. 3 in an exploded view. The modification to the valve 60 is as shown in the rotor 62 of the valve. One of the channels, channel 64A, is lengthened slightly (shown exaggerated) compared to the other channels 64B, 64C. In the example of the Rheodyne 7010 valve, the channel is lengthened approximately 0.25 millimeter (.010 inch). This modification to the valve 60 is typically provided during manufacturing of the valve. Alternatively, a modified rotor 62 can be provided to existing valves, since typically such valves are manufactured with the rotor being readily detachable from the valve body.

Figure 2:
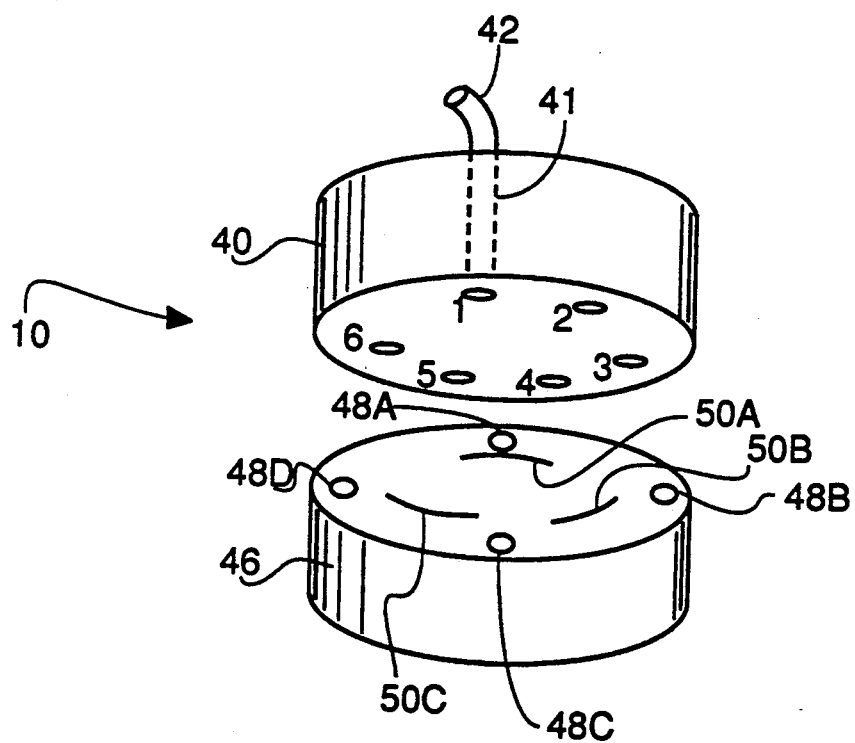
FIG. 2 shows a prior art valve.

The only modification to the valve in the preferred embodiment is to the rotor 62; the valve body 65 is similar to that in the prior art (see FIG. 2) with ports 1, 2, 3, 4, 5, 6 and a passage such as 68 connecting each port such as port 1 to a fitting such as 70. Rotor 62 includes mounting holes 72A, 72B, 72C, 72D. Since the rotor 62 is typically a plastic (or metal) part, it can be easily be machined or molded to have a slightly different length of one channel 64A.

Figure 4:
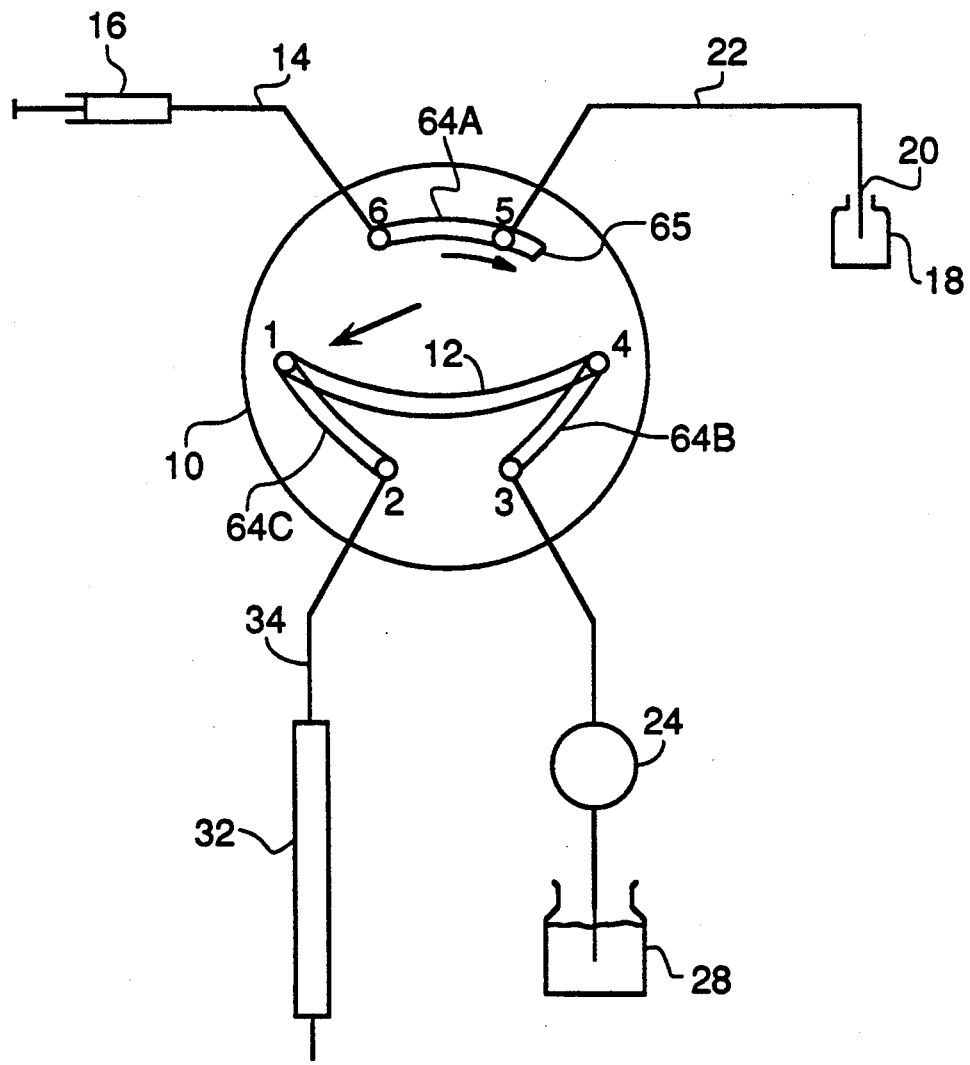
FIG. 4 shows a valve in accordance with the invention in an HPLC system.

FIG. 4 shows a valve 60 as shown in FIG. 3 in use in an HPLC apparatus. FIG. 4 shows valve 60 in the inject position, corresponding to the inject position for the prior art valve 10 shown in FIG. 1B. As shown in FIG. 4, channel 64A is longer than are channels 64B or 64C. Thus, with channel 64 extended on its end 65 where channel 64A converts to needle port 5, it is ensured that the valve 60 when switched to the load position will first connect loop port 4 to needle port 5, before connecting loop port 1 to syringe port 6. This is because the valve rotates in a clockwise direction (as shown by the curved arrow adjacent channel 64A) into the inject position.

Figure 1A:
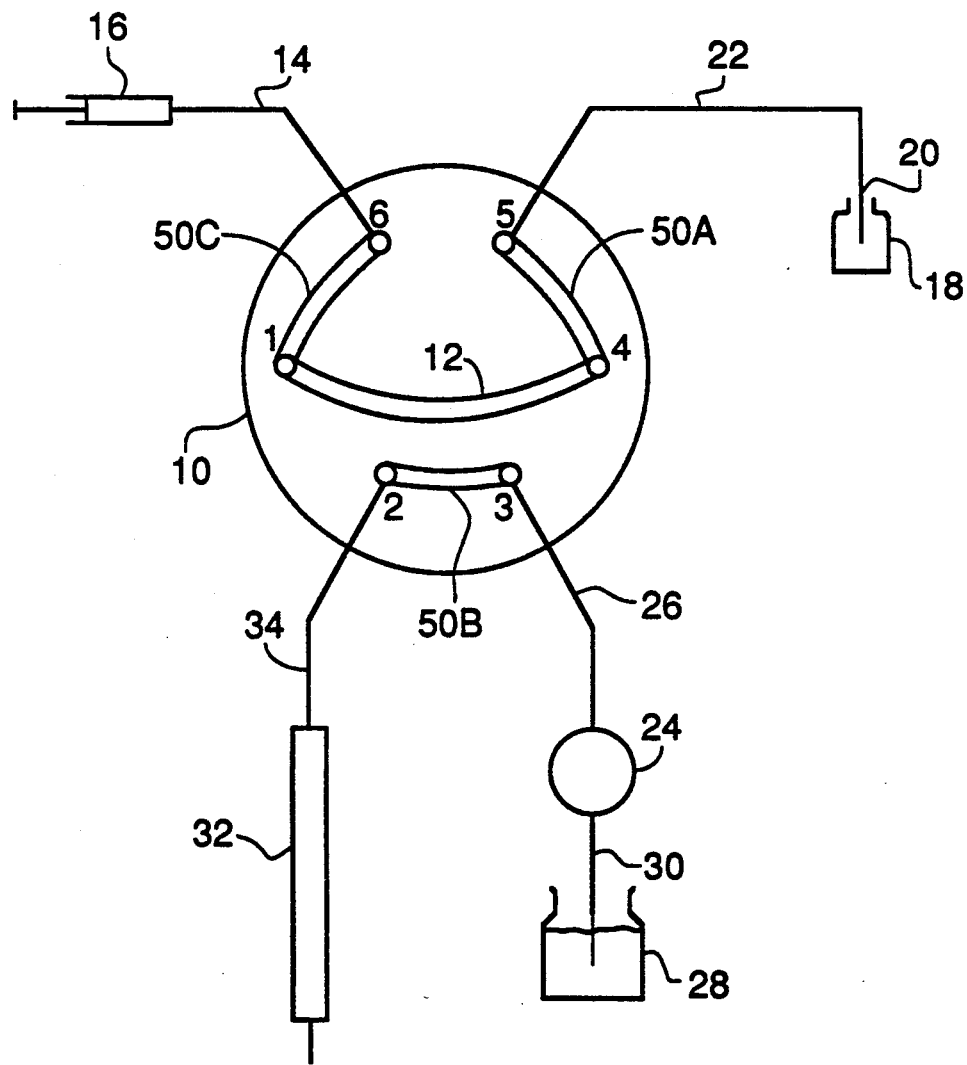
FIGS. 1A and 1B show a prior art valve in an HPLC system.
Figure 1B:
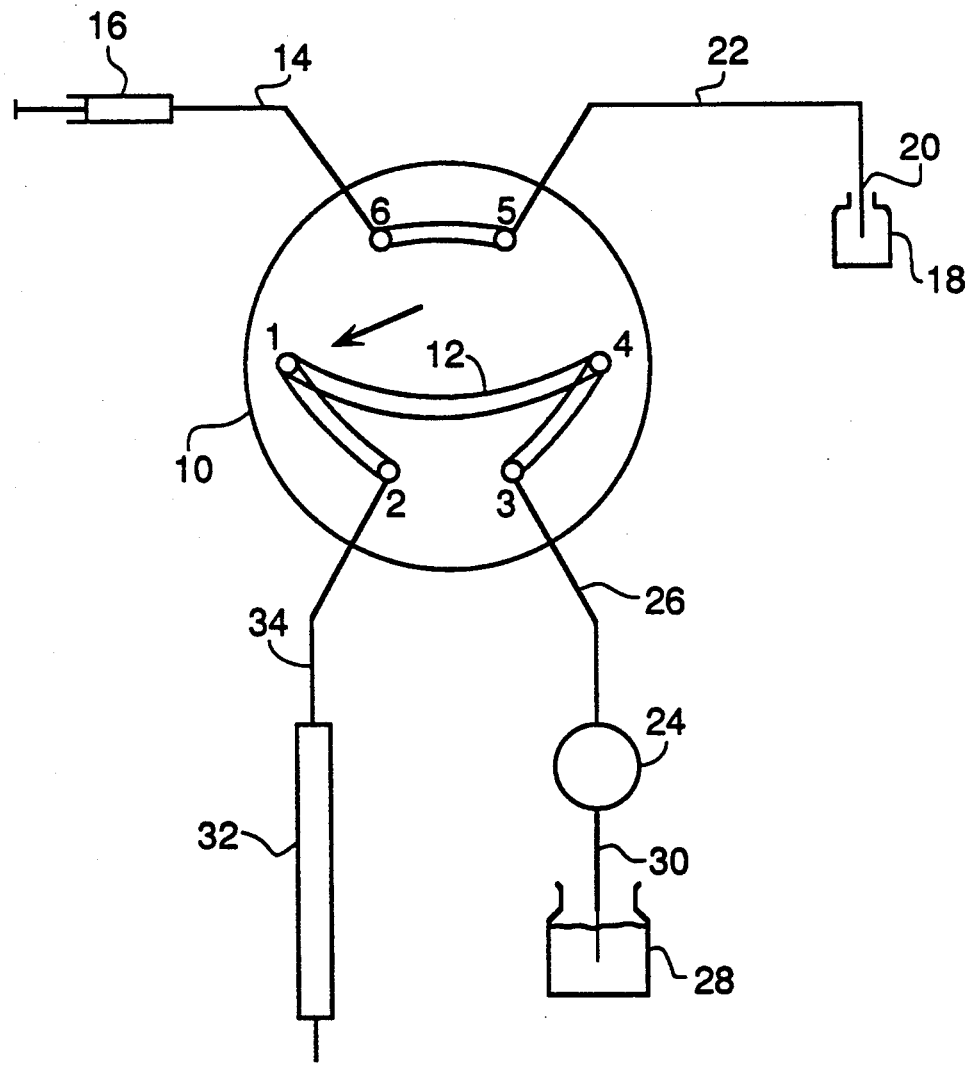

The other elements of the HPLC system shown in FIG. 4 are similar to those shown in FIG. 1B.

Figure 5:
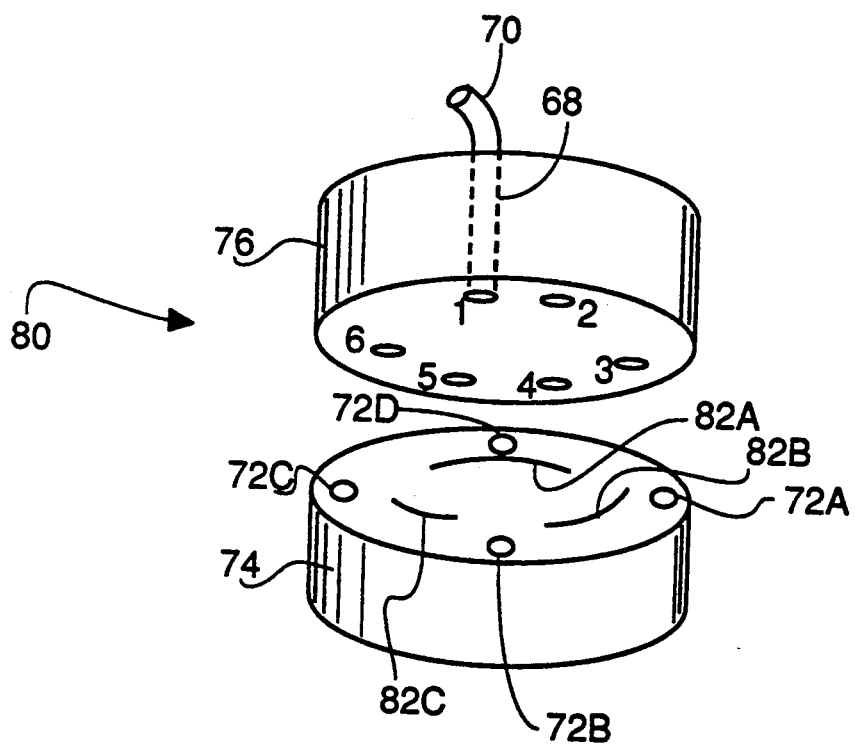
FIG. 5 shows another embodiment of the invention.

In an alternative embodiment of the invention for valve 80 (see FIG. 5), two of the channels 82A, 82B in the valve rotor 74 are made longer than is channel 82C and one of the ports, such as port 1 in the body 76 of the valve 80 is made closer to the adjacent port 2 than is the spacing between the other ports 3, 4, 5, and 6. This arrangement achieves the same effect as the first embodiment to ensure that one of the ports connects before the other in the inject position. The other elements of valve 80 in FIG. 5 are similar to the elements of valve 60 in FIG. 3.

The above description of the invention is illustrative and not limiting; further embodiments will be apparent to one of ordinary skill in the art in the light of the invention.

I claim:

1. A valve comprising:
   at least six ports; and
   at least three non-connected channels, each channel selectively connecting only two ports at any one time;
   wherein a first channel is of a length greater than a length of the two other channels and wherein the ports are arranged symmetrically about a circle, and each of the channels has a shape which is a segment of the circle.

2. The device of claim 1, wherein the length of the first channel is greater than a distance between two ports which are connected by the first channel.

3. A valve comprising:
   a valve body having six ports symmetrically arranged in a circle;
   a loop connecting two of the ports;
   a rotor fitting on the valve body and having three non-connected channels formed therein, each having a shape which is a segment of the circle and juxtaposed to the ports, each channel for connecting two adjacent ports, wherein one of the channels is longer than the other two channels which are of equal length, and the longer channel is longer than a distance along the circle between two adjacent ports.

4. A method of operating a valve having at least six ports connectable by three channels, and having a loop connecting two of the ports, comprising the steps of:
   providing one of the channels longer than the other two channels, which are of equal length;
   operating the valve by rotating the channels so as to connect the ports, and connecting one end of the longer channel to one of the ports before connecting any of the other ports to any one of the channels.

* * * * *